United States Patent [19]

Engländer et al.

[11] Patent Number: 4,465,865

[45] Date of Patent: Aug. 14, 1984

[54] METHOD OF PREPARING TEREPHTHALIC ALDEHYDE AND ISOPHTHALIC ALDEHYDE

[75] Inventors: Fritz Engländer, Bonn; Klaus-Dieter Steffen, Hennef, both of Fed. Rep. of Germany

[73] Assignee: Dynamit Nobel Aktiengesellschaft, Troisdorf, Fed. Rep. of Germany

[21] Appl. No.: 350,905

[22] Filed: Feb. 22, 1982

Related U.S. Application Data

[63] Continuation of Ser. No. 179,589, Aug. 21, 1980, abandoned.

[30] Foreign Application Priority Data

Aug. 28, 1979 [DE] Fed. Rep. of Germany ....... 2934614

[51] Int. Cl.$^3$ .............................................. C07C 45/00
[52] U.S. Cl. ..................................... 568/436; 570/196
[58] Field of Search ........................................... 568/436

[56] References Cited

U.S. PATENT DOCUMENTS

| | | | |
|---|---|---|---|
| 3,081,347 | 3/1963 | Leary | 568/436 X |
| 4,085,147 | 4/1978 | Rosinger et al. | 568/436 |
| 4,108,904 | 8/1978 | Brown et al. | 568/436 |
| 4,206,152 | 6/1980 | Gosteli | 568/436 X |

*Primary Examiner*—Bernard Helfin
*Attorney, Agent, or Firm*—Sprung, Horn, Kramer & Woods

[57] ABSTRACT

A method of preparing terephthalic aldehyde or isophthalic aldehyde from p-xylene or m-xylene, which comprises chlorinating the side chain or p or m xylene to a chlorination degree of 2.5 to 3.5, and thereafter contacting the so-chlorinated product with hexamethylenetetramine in aqueous solution at elevated temperature whereby the corresponding aldehyde is obtained.

9 Claims, No Drawings

METHOD OF PREPARING TEREPHTHALIC ALDEHYDE AND ISOPHTHALIC ALDEHYDE

This is a continuation of application Ser. No. 179,589, filed Aug. 21, 1980 and now abandoned.

BACKGROUND OF THE INVENTION

1. Field of the Invention

The invention relates to a method of preparing terephthalic dialdehyde and isophthalic dialdehyde.

2. Discussion of Prior Art

For the sake of simplicity the following abbreviations will be used herein:
p-100=p-methylbenzyl chloride*
p-200=p-methylbenzal chloride**
p-101=1,4-bis-(chloromethyl)benzene
p-201=1-dichloromethyl-4-chloromethylbenzene
p-202=1,4-bis-(dichloromethyl)benzene
p-302=1-trichloromethyl-4-dichloromethylbenzene.
*or p-chloromethyl benzene **or p-dichloromethyl benzene The preparation of a number of aldehydes can be performed through a reaction of the corresponding —CH$_2$Cl compounds with hexamethylenetetramine, while other aldehydes obviously cannot be obtained in this manner.

One possibility for the preparation of the terephthalic aldehyde consists in the reaction of pure 1,4-bis-(chloromethyl)benzene with hexamethylenetetramine, but it results in yields of only 34% of the theory.

This method has a number of additional disadvantages: The side-chain chlorination of p-xylene is not selective, and instead the various possible chlorination stages are obtained together. The ratio of the individual chlorination products depends exclusively on the degree of chlorination. The amount of 1,4-bis-(chloromethyl)benzene passes during chlorination through a maximum which occurs at 46 wt-% Cl and a chlorination degree of 2.4. The largest percentage of p-101 is therefore present when the degree of chlorination* has already far exceeded a value of 2.0 for pure p-101. Upon further chlorination, 1,4-bis-(chloromethyl)benzene decreases again in favor of the formation of, for example, 1,4-bis-(dichloromethyl)benzene and more highly chlorinated xylenes.
*the degree of chlorination being befined as the number of chlorine atoms in the side chains of a molecule of a substance or a mixture thereof.

Accordingly, the separation of 1,4-bis-(chloromethyl)benzene from the six-component mixture is difficult, inasmuch as the boiling points are close together.

SUMMARY OF THE INVENTION

Now it has been found that these disadvantages can be considerably reduced by using the mixture of compounds that forms upon the chlorination of p-xylene or m-xylene, without further separation, for the reaction to terephthalic aldehyde.

The subject matter of the invention is a method of preparing terephthalic aldehyde or isophthalic aldehyde from p-xylene or m-xylene, which is characterized by contacting the chlorinated xylene having a chlorination degree of 2.5 to 3.5 with hexamethylenetetramine in aqueous solution at elevated temperature and obtaining the aldehyde.

Ring chlorination can be avoided by known methods as exclosure of metals and metal salt traces, above all that of iron, by distilling the xylene used as raw material or addition of complexing agents as hexamethylenetetramine (0,1 to 2,0 wt.-% of the xylene) during the chlorination.

The degree of chlorination of the chlorination mixtures is to be calculated in a known manner by multiplying the chlorination degree of the contained substances, i.e., for example, 1 for p- (or m)-100 or 2 for p-101 and p-200, by the analytically determined content of these substances in weight-percent in the chlorination mixture, adding the values obtained and dividing by the sum of the contents.

The degree of chlorination is to be preferably 2.6 to 3.1. The amount of hexamethylenetetramine can be stoichiometric or an excess, the term stoichiometric being considered to mean that one mole of hexamethylenetetramine is used per mole of —CH$_2$Cl group. As the excess of hexamethylene tetramine increases, the aldehyde yield increases. Excesses amounting to more than 30%, however, do not further improve the economy of the process. The hexamethylenetetramine excess therefore generally amounts to from 0 to 30 wt-%, and preferably to 10 to 20 wt-%.

Instead of hexamethylenetetramine, an aqueous solution of ammonia and formaldehyde can be used, thereby obtaining similar results, evidently on account of the chemical equilibrium in aqueous solution between hexamethylenetetramine and the ammonia-formaldehyde mixture. The quantity ratio of the ammonia and formaldehyde is generally to be in accord with the 4:6 molar ratio of hexamethylenetetramine, but it can vary by up to 10% on either side. Generally the mole ratio of ammonia to formaldehyde is 0,55 to 0,90:1.

After hydrolysis, the product is obtained by filtering it out and washing out the water-soluble salts. Refinment is achieved by distillation, or, if desired, crystallation or sublimation.

The reaction of the chloroxylene mixture with hexamethylenetetramine takes place at temperatures of 70° to 140° C., preferably at 100° to 115° C. at a pressure of 1 bar to 5 bars absolute with atmospheric pressure preferred. Generally the reaction is performed for at 100 360 minutes, preferably 100 to 180 minutes, depending on the reaction temperature.

The invention can be performed in the absence of a catalyst.

Surprisingly, the aldehyde yields obtained by the use of the chlorination mixture was substantially higher than when the starting product is pure p-101.

The yields of aldehyde amount to as much as 77% with respect to the p-xylene or m-xylene starting product.

The present method therefore permits a simplified synthesis of the not easily accessible substances terephthalic and isophthalic aldehyde, in a greatly improved total yield.

The chlorination mixture is prepared by the radical chlorination of xylene. This can be done in a solvent, such as carbon tetrachloride, trichloroethane, for example, or also without solvent. The reaction temperature of 50° to 150° C., preferably 80° to 90° C., at a pressure of 1 bar to 2 bars absolute. The temperature is adjusted such that the reaction mixture will be in the molten state. The radicals needed for the reaction can be produced either by irradiation with ultra-violet light or by the addition of radical formers such as azo-bis-diisobutyronitrile, for example. Other radical formers include organic peroxides as dibenzoylperoxide.

The chlorination is, of course, to be conducted so that products chlorinated in the nucleus form in only very small amounts.

In the chlorination mixture, p-100 and p-302 are to be present in amounts of not more than 1%, since they lead to yield losses. p-Toluic aldehyde forms from p-100 during the reaction, and terephthalic aldehydic acid forms from p-302. The dialdehydes prepared can be used in a known manner for numerous purposes. Particularly terephthalic aldehyde finds many uses as an intermediate for organic syntheses, such as the preparation of optical brighteners and dyes, pharmaceutical products and compounds for combatting viruses, bacteria, fungi and insects.

EXAMPLES

EXAMPLE 1

Chlorination of p-xylene:

p-Xylene (100 g=0.943 mol) is chlorinated at a temperature of 80° to 90° C. under radiation from an ultraviolet lamp. 189.7 g of chlorination mixture is obtained, which has the following product composition (in wt-%): p-100 0.3, p-200 1.6, p-101 32.9, p-102 51.9, p-202 12.1, p-302 0.8.

Conversion to the aldehyde:

189.7 g of chlorination mixture (chlorination degree 2.79), 166.8 g of hexamethylenetetramine and 630 g of water are heated with reflux for 6 hours with vigorous stirring. The reaction mixture is cooled and the aldehyde is isolated by filtration. After drying, a light-yellow raw product is obtained, which can be further purified by distillation or sublimation.

The yield of pure product amounts to 86.5 g corresponding to a yield of 68.4% with respect to the p-xylene put in. The aldehyde had a purity of 98.7% as determined by gas chromatography.

EXAMPLE 2

189.7 g of chlorination mixture as in Example 1 is kept together with 166.8 g of hexamethylenetetramine and 630 g of water at a temperature of 110° C. for two hours with vigorous stirring. After cooling, and isolating and distilling the raw product, 88 g of terephthalic aldehyde is obtained in a purity of 98.1%, corresponding to a yield of 69.6% of the p-xylene starting product.

EXAMPLE 3

Example 2 is repeated, but with 216.3 g of hexamethylenetetramine, corresponding to a 30% excess. 97.7 of terephthalic aldehyde is obtained, with a purity of 97.8%, corresponding to a yield of 77.3% with respect to the p-xylene starting product.

EXAMPLE 4

189.7 g of chlorination mixture as in Example 1 is added to a mixture of 612 g of a 35% formalin solution, and 272 g of a 29.8% ammonia solution. The mixture is refluxed for 6 hours and vigorously stirred.

After processing by conventional methods, 82 g of terephthalic aldehyde is obtained with a purity of 98%, corresponding to a yield of 64.9% with respect to the p-xylene put in.

EXAMPLE 5

Chlorination of m-xylene:

m-Xylene (100 g=0.943 mol) is chlorinated at a temperature of 60° to 80° C. under radiation from an ultraviolet lamp. 187.6 g of chlorination mixture is obtained having the following product composition (wt-%): m-100 2.0%, m-101 46.0%, m-201 39.2%, m-202 11.2%.

Conversion to the aldehyde:

187.6 g of chlorination mixture (degree of chlorination 2.61), 227 g of hexamethylenetetramine and 625 g of water are heated at 110° C. with stirring, for two hours. After cooling to 100° C., the mixture is acidified with 30% hydrochloric acid to pH 1 and is refluxed for 10 minutes. The reaction mixture is cooled and the aldehyde is isolated by filtration. The raw product obtained after drying is purified by distillation. The yield amounts to 83.8 g, corresponding to 66.3% with respect to the m-xylene starting product.

EXAMPLE 6

By the chlorination of p-xylene a chlorination mixture is obtained having a chlorination degree of 3.01 and having the following composition (in wt-%): 100 0.23, 200 1.2, 101 18.8, 201 50.3, 301 3.6, 202 21.6, 302 4.13, 303 0.07.

170 kg of this chlorination mixture, 134 kg of hexamethylenetetramine and 510 liters of water are heated for 2 hours at 115° C. with stirring. After filtering out the raw product and distillation, 66.4 kg of terephthalic aldehyde is obtained, i.e., 61.1% of the theory with respect to p-xylene.

What is claimed is:

1. A method for preparing terephthalic aldehyde or isophthalic aldehyde from p-xylene or m-xylene, which comprises chlorinating the side chain of p or m xylene to a chlorination degree of 2.5 to 3.5, said chlorination degree being defined as the number of chorine atoms in the side chain of a molecule or a mixture of said molecules, and thereafter contacting the so chlorinated product with hexamethylenetetramine which hexamethylenetetramine is present and is present in a stoichiometric excess of up to 30% in an aqueous solution which solution consists essentially of said chlorinated p or m-xylene, said hexamethylenetetramine and water, at 70° to 140° C. whereby the corresponding aldehyde is obtained.

2. Method of claim 1, wherein the reaction with hexamethylenetetramine is performed without isolating the chlorinated xylene.

3. Method of claim 1, wherein the 10–20% stoichiometric excess of hexamethylenetetramaine is employed.

4. A process according to claim 1, wherein p-xylene is chlorinated to a chlorination degree of 2.5 to 3.5.

5. A process according to claim 6, wherein p-xylene is chlorinated to a chlorination degree of 2.5 to 3.5.

6. A process according to claim 1, wherein p-xylene is chlorinated.

7. A process according to claim 1, wherein m-xylene is chlorinated.

8. A method of preparing terephthalic aldehyde or isophthalic aldehyde from p-xylene or m-xylene which comprises chlorinating the side chain of m or p-xylene to a chlorination degree of 2.5 to 3.5 and thereafter contacting the so chlorinated product with a mixture of formaldehyde and ammonia in water.

9. A method according to claim 8 wherein the formaldehyde is present in the reaction mixture in at least a stoichiometric amount and up to 30 wt.-percent excess and said ammonia is present in at least a stoichiometric amount of up to 30 wt.-percent excess.

* * * * *